(12) United States Patent
Sánchez García et al.

(10) Patent No.: US 7,776,519 B2
(45) Date of Patent: Aug. 17, 2010

(54) USE OF THE SLUG GENE, OR OF THE TRANSCRIPTION OR EXPRESSION PRODUCTS THEREOF IN THE DETECTION AND/OR TREATMENT OF CANCEROUS CELLS

(75) Inventors: Isidro Sánchez García, Salamanca (ES); Alberto Orfao De Matos, Salamanca (ES); Jesús Perez Losada, Salamanca (ES)

(73) Assignees: Universidad de Salamanca, Salamanca (ES); Consejo Superior de Investigaciones Cientificas, Madrid (ES)

( * ) Notice: Subject to any disclaimer, the term of this patent is extended or adjusted under 35 U.S.C. 154(b) by 538 days.

(21) Appl. No.: 10/466,817

(22) PCT Filed: Jan. 23, 2002

(86) PCT No.: PCT/ES02/00026

§ 371 (c)(1),
(2), (4) Date: Dec. 21, 2005

(87) PCT Pub. No.: WO02/059361

PCT Pub. Date: Aug. 1, 2002

(65) Prior Publication Data

US 2006/0141454 A1    Jun. 29, 2006

(30) Foreign Application Priority Data

Jan. 23, 2001   (ES)  ................................. 200100151

(51) Int. Cl.
C12Q 1/00    (2006.01)
C12Q 1/68    (2006.01)
G01N 33/567  (2006.01)
G01N 33/574  (2006.01)

(52) U.S. Cl. .............................. 435/4; 435/6; 435/7.21; 435/7.23

(58) Field of Classification Search .................. None
See application file for complete search history.

(56) References Cited

U.S. PATENT DOCUMENTS

2006/0019256 A1* 1/2006 Clarke et al. .................... 435/6

OTHER PUBLICATIONS

Freshney (Culture of Animal Cells, A Manual of Basic Technique, Alan R. Liss, Inc., 1983, New York, p. 4).*
Dermer (Bio/Technology, 1994, 12:320).*
Drexler et al (Leukemia and Lymphoma, 1993, 9:1-25).*
Zellner et al (Clin. Can. Res., 1998, 4:1797-1802).*
Embleton et al (Immunol Ser, 1984, 23:181-207).*
Zips et al (In vivo, 2005, 19:1-7).*
Busken, C et al, (Digestive Disease Week Abstracts and Itinerary Planner, 2003, abstract No. 850).*
Kaiser (Science, 2006, 313, 1370).*
Krontiris and Capizzi (Internal Medicine, 4th Edition, Editor-in-chief Jay Stein, Elsevier Science, 1994 Chapters 71-72, pp. 699-729).*
(Khan et al., Proc. Natl. Acad. Sci. USA 96: 13264-13269 (1999)).*
Boyd (The Basic Science of Oncology, 1992, McGraw-Hill, Inc., p. 379).*
Stites et al (Basic and Clinical Immunology, 9th Ed, Appleton and Lange, Norwalk, 1997, p. 250-251).*
Nieto (Nature Reviews Cell Biology, Mar. 2002, 3:155-166).*
Khan et al. (Proc. Natl. Acad. Sci. USA, Nov. 9, 1999 96: 13264-13269).*
ATCC No. CRL-1990 (Schneider et al. 1977).*
Ralph et al. (J. Exp. Med. 1976, 143: 1528-1533).*
Cohen, M.E. et al. "Human SLUG gene organization, expression, and chromosome map location on 8q" Genomics, 1998, vol. 51, pp. 468-471.
Hemavathy, K. et al. "Human Slug is a repressor that localizes to sites of active transcription ," Molecular and Cellular Biology, 2000, vol. 26, No. 14, pp. 5087-5095.
Hemavathy, K. et al. "Snail/Slug family of repressors: Slowly going into the fast lane of development and cancer," Gene,2000, vol. 257, pp. 1-12.
Inukai, T. et al. "Identification of the antiapoptotic zinc-finger transcription factor SLUG as a downstream target of E2A-HLF oncogemc fusion protein." "40th Annual Meeting of the American Society of Hematology; Miami Beach, Florida, USA; Dec. 4-8, 1998." Published in Blood, 1998, No. 10, suppl. 1 part 1-2, p. 479 A.
Inukai, T. et al. "Slug, a ces-1-related zinc finger transcription factor gene with antiapoptotic activity, is a downstream target of the E2A—HLF oncoprotein," Molecular Cell, 1999, vol. 4, pp. 343-352.
Savagner, P. et al. "The zinc-finger protein Slug causes desmosome dissociation,an initial and necessary step for growth factor-induced epithelial-mesenchymal transition ," The Journal of Cell Biology, 1997, vol. 137, No. 6, pp. 1403-1419.
Seidel M.G. et al. "E2A-HLF usurps control of evolutionarily conserved survival pathways," Oncogene, 2001, vol. 20, pp. 5718-5725.
Stegmann, K. et al. "Human transcription factor SLUG mutation analysis in patients with neural tube defects and identification of a missense mutation(D119E) in the slug subfamily defining region," Mutation Research Genomics, 1999, vol. 406, pp. 63-69.

* cited by examiner

Primary Examiner—Peter J Reddig
(74) Attorney, Agent, or Firm—Sullivan & Worcester LLP; Christopher T. McWhinney

(57)    ABSTRACT

Method for the detection of cancerous cells, in particular, mesenchymal tumoral cells, in a biological sample suspected of containing said malignant cells. The methods are based on the aberrant expression of the Slug gene or transcription or expression products thereof. Also disclosed are methods of treatment that based on the alteration of the transcription or expression of the Slug gene and methods for screening the compounds that have cancer treating activities. Pharmaceutical compositions comprising the anti-cancer compounds are also disclosed.

8 Claims, 9 Drawing Sheets

SEQUENCE LISTING

<160> NUMBER OF SEQ ID NOS: 14

<210> SEQ ID NO 1
<211> LENGTH: 24
<212> TYPE: DNA
<213> ORGANISM: Artificial
<220> FEATURE:
<223> OTHER INFORMATION: Oligonucleotide primer

<400> SEQUENCE: 1
agcactctcc agcctctcac cgca                                          24

<210> SEQ ID NO 2
<211> LENGTH: 12
<212> TYPE: DNA
<213> ORGANISM: Artificial
<220> FEATURE:
<223> OTHER INFORMATION: Oligonucleotide primer

<400> SEQUENCE: 2
gatctgcggt ga                                                       12

<210> SEQ ID NO 3
<211> LENGTH: 24
<212> TYPE: DNA
<213> ORGANISM: Artificial
<220> FEATURE:
<223> OTHER INFORMATION: Oligonucleotide primer

<400> SEQUENCE: 3
accgacgtcg actatccatg aaca                                          24

<210> SEQ ID NO 4
<211> LENGTH: 12
<212> TYPE: DNA
<213> ORGANISM: Artificial
<220> FEATURE:
<223> OTHER INFORMATION: Oligonucleotide primer

<400> SEQUENCE: 4
gatctgttca tg                                                       12

<210> SEQ ID NO 5
<211> LENGTH: 24
<212> TYPE: DNA
<213> ORGANISM: Artificial
<220> FEATURE:
<223> OTHER INFORMATION: Oligonucleotide primer

<400> SEQUENCE: 5
aggcaactgt gctatccgag ggaa                                          24

<210> SEQ ID NO 6
<211> LENGTH: 12
<212> TYPE: DNA
<213> ORGANISM: Artificial
<220> FEATURE:
<223> OTHER INFORMATION: Oligonucleotide primer

<400> SEQUENCE: 6
gatcttccct cg                                                       12

<210> SEQ ID NO 7
<211> LENGTH: 20

```
<212> TYPE: DNA
<213> ORGANISM: Artificial
<220> FEATURE:
<223> OTHER INFORMATION: Oligonucleotide primer

<400> SEQUENCE: 7
gcctccaaaa agccaaacta                                               20

<210> SEQ ID NO 8
<211> LENGTH: 20
<212> TYPE: DNA
<213> ORGANISM: Artificial
<220> FEATURE:
<223> OTHER INFORMATION: Antisense oligonucleotide primer

<400> SEQUENCE: 8
cacagtgatg gggctgtatg                                               20

<210> SEQ ID NO 9
<211> LENGTH: 20
<212> TYPE: DNA
<213> ORGANISM: Artificial
<220> FEATURE:
<223> OTHER INFORMATION: Oligonucleotide primer

<400> SEQUENCE: 9
gtatcatctg actttgagcc                                               20

<210> SEQ ID NO 10
<211> LENGTH: 20
<212> TYPE: DNA
<213> ORGANISM: Artificial
<220> FEATURE:
<223> OTHER INFORMATION: Antisense oligonucleotide primer

<400> SEQUENCE: 10
gtaccaggag tgtttctcca                                               20

<210> SEQ ID NO 11
<211> LENGTH: 24
<212> TYPE: DNA
<213> ORGANISM: Artificial
<220> FEATURE:
<223> OTHER INFORMATION: Internal probe

<400> SEQUENCE: 11
gacacacata cagtgattat ttcc                                          24

<210> SEQ ID NO 12
<211> LENGTH: 21
<212> TYPE: DNA
<213> ORGANISM: Artificial
<220> FEATURE:
<223> OTHER INFORMATION: Internal probe

<400> SEQUENCE: 12
taactaaagg tgaaaagctc c                                             21

<210> SEQ ID NO 13
<211> LENGTH: 20
<212> TYPE: DNA
<213> ORGANISM: Artificial
<220> FEATURE:
<223> OTHER INFORMATION: Oligonucleotide primer

<400> SEQUENCE: 13
```

```
atgccgcgct ccttcctggt                                          20
```

<210> SEQ ID NO 14
<211> LENGTH: 20
<212> TYPE: DNA
<213> ORGANISM: Artificial
<220> FEATURE:
<223> OTHER INFORMATION: Oligonucleotide primer

<400> SEQUENCE: 14

```
tcagtgtgcc acacagcagc                                          20
```

US 7,776,519 B2

USE OF THE SLUG GENE, OR OF THE TRANSCRIPTION OR EXPRESSION PRODUCTS THEREOF IN THE DETECTION AND/OR TREATMENT OF CANCEROUS CELLS

FIELD OF THE INVENTION

The invention relates to the use of the Slug gene for detecting the presence of cancerous cells in a biological sample, based on the aberrant expression of said Slug gene, or transcription or expression products thereof. The invention also relates to the use of the Slug gene, or transcription or expression products thereof (RNA or proteins) in the treatment of cancer.

BACKGROUND OF THE INVENTION

The recent advances in the treatment of cancer have shown that in order to plan a suitable cancer treatment and to determine a precise prognosis, it is necessary to have sensitive methods available for detecting the presence of cancer, the type of cancer and the stage thereof in order to determine its specific location and its possible spread to other tissues. A precise diagnosis of the cancer can contribute to a reduction in the number of deaths due to this disease and improve the quality of life of patients, given that it allows the most appropriate treatment to be chosen (chemotherapy, surgical removal, etc.) and helps reduce the inconveniences for the patient by defining the end point of the therapeutic treatment.

The prognostic markers provide important information for the treatment and development of cancer in patients. In fact, for the application of systemic adjuvant therapy in the treatment of some types of primary cancers, identification of patients at high and low risk is one of the main goals. Several prognostic markers are known, both classical, such as tumor size, state of lymph nodule, histopathology, state of steroid receptor, and second generation markers, such as rate of proliferation, DNA ploidy, oncogenes, growth factor receptors and some glycoprotein receptors, which are useful for taking therapeutic decisions (McGuire, W. L., Prognostic Factors for Recurrence and Survival, in "Educational Booklet American Society of Clinical Oncology," 25th Annual Meeting, 89-92 (1989); Contesso et al., Eur. J. Clin. Oncol., 25: 403-4'9 (1989)). Although none of the known prognostic markers completely satisfy the objective of distinguishing between patients of high and low risk, the combination of different markers can improve the prediction of the prognosis of the patient, and so the search continues for new prognosis markers that can be added to the current ones to aid in the corroboration of the prognosis of the cancer, its progression and the residual disease after treatment.

On the other hand, most of the methods used for the detection of cancerous cells have a limited sensitivity, although the molecular methods based on analysis of nucleic acids have improved said sensitivity (Burchill S. A. & Selby P. J., J. Pathol. 190: 6-14 (2000)). Nevertheless, none of these strategies allows an invasive tumor cell to be distinguished from a non-invasive tumor cell.

The Slug gene is a gene present in vertebrates. It codes for a transcription factor of the "zinc fingers" type (SLUG), implicated in epithelial-mesenchymal transitions (Nieto et al., Science 264: 835-849 (1994)).

BRIEF DESCRIPTION OF THE INVENTION

The invention addresses, in general, the problem of finding a marker for the detection of cancerous cells, such as mesenchymal tumor cells.

The solution provided by this invention is based on the fact that the inventors have surprisingly discovered that expression of the Slug gene is related to the presence of cancerous cells, such as mesenchymal tumor cells, as they have been able to observe that malignant cells express significantly high levels of the Slug gene and/or of its transcription and expression products when they are compared to normal cells. Different trials performed by the inventors have shown that the product of the SLUG gene is expressed in cells of tissue samples that present mesenchymal tumor cells but it is not expressed, or expressed at almost inappreciable levels, in samples of normal tissues. In a particular embodiment, the inventors have observed that the Slug gene regulates the disseminative capacity of the leukemia cells with BCR-ABL, which indicates that said Slug gene plays a role in tumor invasion.

Among the possible applications derived from the aforementioned discovery is the possibility of using the Slug gene, or transcription or expression products thereof, for detecting tumor invasiveness and/or as a therapeutic target in the treatment of cancer.

Therefore, an object of this invention constitutes a method for detecting the presence of cancerous cells in a test sample based on the evaluation of the expression of the Slug gene or transcription or expression products thereof (RNA or protein).

An additional object of this invention constitutes the use of the Slug gene or transcription or expression products thereof, as a therapeutic target in the treatment of cancer.

BRIEF DESCRIPTION OF THE FIGURES

FIG. 1A shows the result of Northern blot analysis of total RNA isolated from Ba/F3 (band 1), Ba/F3+p190 (band 2) and Ba/F3+p210 (band 3) cells. Control experiments were performed on Ba/F3 cells transfected with an empty vector. The nylon membrane was hybridized with a fragment of SLUG cDNA and then purified and rehybridized with a β-actin probe. FIG. 1B shows the result of Northern blot analysis of total RNA isolated from Ba/F3+Combi p190 cells developed in the absence (band 1) or presence of tetracycline (band 2), Ba/F3+p190 (band 2) and Ba/F3 control cells (band 3). The blot was hybridized with SLUG cDNA fragments, Bcl-2 and myc, and then purified and rehybridized with a β-actin probe.

FIG. 2A shows the result of Northern blot analysis of total RNA isolated from different mouse tissues [lung, (PB) peripheral blood, heart, testicle, brain, intestine, kidney, muscle, liver, spleen, thymus and BM (bone marrow)], hybridized with a Slug cDNA probe and then purified and rehybridized with a β-actin probe. The mobility of the 28S and 18S RNA are indicated (PB, peripheral blood; BM, bone marrow). FIG. 2B illustrates the expression of SLUG mRNA in BCR-ABLP[190] and BCR-ABLP[210] transgenic mice and collects the results from Northern blot analysis of total RNA isolated from peripheral blood of control mice (band 1), and from BCR-ABLP[190] transgenic mice (bands 2 to 4) and BCR-ABLP210 transgenic mice (bands 5 to 6), hybridized with a cDNA probe and then purified and rehybridized with a β-actin probe. The mobility of the 28S and 18S RNA are indicated.

FIG. 4A shows the result of Northern blot analysis of total RNA isolated from Ba/F3 cells transfected with SLUG cDNA from mouse (band 1) and Ba/F3 control cells (band 2). The nylon membrane is hybridized with a fragment of SLUG cDNA and then purified and rehybridized with a probe of β-actin. FIG. 4B is a graph that illustrates the survival of Ba/F3 cells that express the SLUG protein in absence of IL-3. The cells that grew exponentially in supplemented medium with IL-3 were adjusted to $5 \times 10^5$ cells/ml on day 0 and were then cultured after elimination of IL-3. The number of viable cells is shown for the Ba/F3 cells transfected with BCR-ABL and with SLUG in the absence of IL-3. FIG. 4C illustrates that cell death is accompanied by the appearance of the DNA ladder by internucleosomal cleavage after deprivation of IL-3. Low molecular weight DNA was isolated 24 hours after deprivation of IL-3 from Ba/F3 +Slug cells (band 1), Ba/F3+p210 cells (band 2), Ba/F3+p190 cells (band 3) and from control Ba/F3 cells (band 4). The DNA was labeled terminally, resolved by 2% agarose gel electrophoresis and developed by autoradiography.

FIG. 5A shows the results of the isolation of total RNA from Ba/F3+p210 cells (band 1) and Ba/F3+p190 cells (band 2) transfected with a vector that expressed the Slugh gene (Slug gene of mouse) without sense. The cellular RNA was hybridized with a cDNA probe of mouse Slugh. The filter was denatured and rehybridized with ABL and β-actin. FIG. 5B shows the result of the hybridization of Northern filter of Ba/F3 cells that expressed transfected BCR-ABL (band 1, Ba/F3+p210+ASlug; band 3, Ba/F3+p190+ASlug) and non-transfected (bands 2, Ba/F3+p210; band 4, Ba/F3+p190). As a probe, an antisense Slugh oligonucleotide that comprises the first 49 bases of the sequence coding for Slugh cDNA of mouse was used. FIG. 5C illustrates that the lymphoid and myeloid differentiation specific to the B cells induced in Ba/F3 cells by BCR-ABLP$^{190}$ and BCR-ABLP$^{210}$ oncogenes, respectively, is not influenced by the suppression of Slug. In FIG. 5C, the expression profiles are shown of Ba/F3+ p190 cells (upper left panel) Ba/F3+p190+antisense Slug (upper right panel), Ba/F3+p210 (lower left panel) and Ba/F3+p210+antisense Slug (lower right panel). The cells were stained with B220 monoclonal antibodies (specific B cell marker) and Gr-1 (specific marker of myeloids) and they were analyzed by flow cytometry.

FIG. 7A shows the result of a macroscopic analysis of tumors induced by Ba/F3+p190 cells, while FIGS. 7B and 7C show the histological aspect of the tumors induced in naked mice. The section stained with hematoxylin-eosin of the mouse tumor developed after injection of the Ba/F3+p190 cells in which the expression of Slug had be specifically suppressed (FIG. 7C). The Ba/F3+p190 cells that express Slugh disobey the social order of organ boundaries and migrate as individual cells, producing metastasis in different regions. Similar results were observed in multiple sections of the two tumors. The images of FIGS. 7B and 7C are amplified 40 times.

FIG. 8A shows that in the haematopoietic system, the normal, non-committed, progenitor cells with capacity for self-renewal are differentiated from the mature cells. During this transition, the expression of Slug is down regulated. These normal non-committed progenitor cells are responsible for signals of the medium that regulate the number of mature cells produced and limit the self-renewal of the primitive cells. When, in physiological situations, these normal, non-committed progenitor cells migrate, the Slug gene could promote their survival, allowing them to perform their function. If this is not achieved in a specific period of time, they will undergo apoptosis, as they have been denied the necessary external signals. In FIG. 8B, the situation is illustrated in the case of leukemogenesis; in this case, the target cell in which there is a chromosomal abnormality is a non-committed progenitor (Cobaleda et al., Blood 95: 1007-1113 (2000); Sánchez-García et al., Current Genomics, 1: 71-80 (2000)). As a result, the differentiation of the target cell is blocked, but the inhibition of the differentiation is not sufficient for the transformation, because the survival and proliferation of the target cells would be restricted to a particular microenvironment. Thus, there must be other genetic changes that allow the growth of the cells outside their normal environment, in addition to mutations that block differentiation. The fusion oncogenes associated with mesenchymal cells (both leukemias and solid tumors) block differentiation and have the capacity to activate target genes such as Slug that promote survival (regardless of the external signals required) and the migration of the defective target cells to different environments. These data reinforce the idea that the transformation may occur as a result of the creation/activation of a single oncogene.

DETAILED DESCRIPTION OF THE INVENTION

Figure 1:
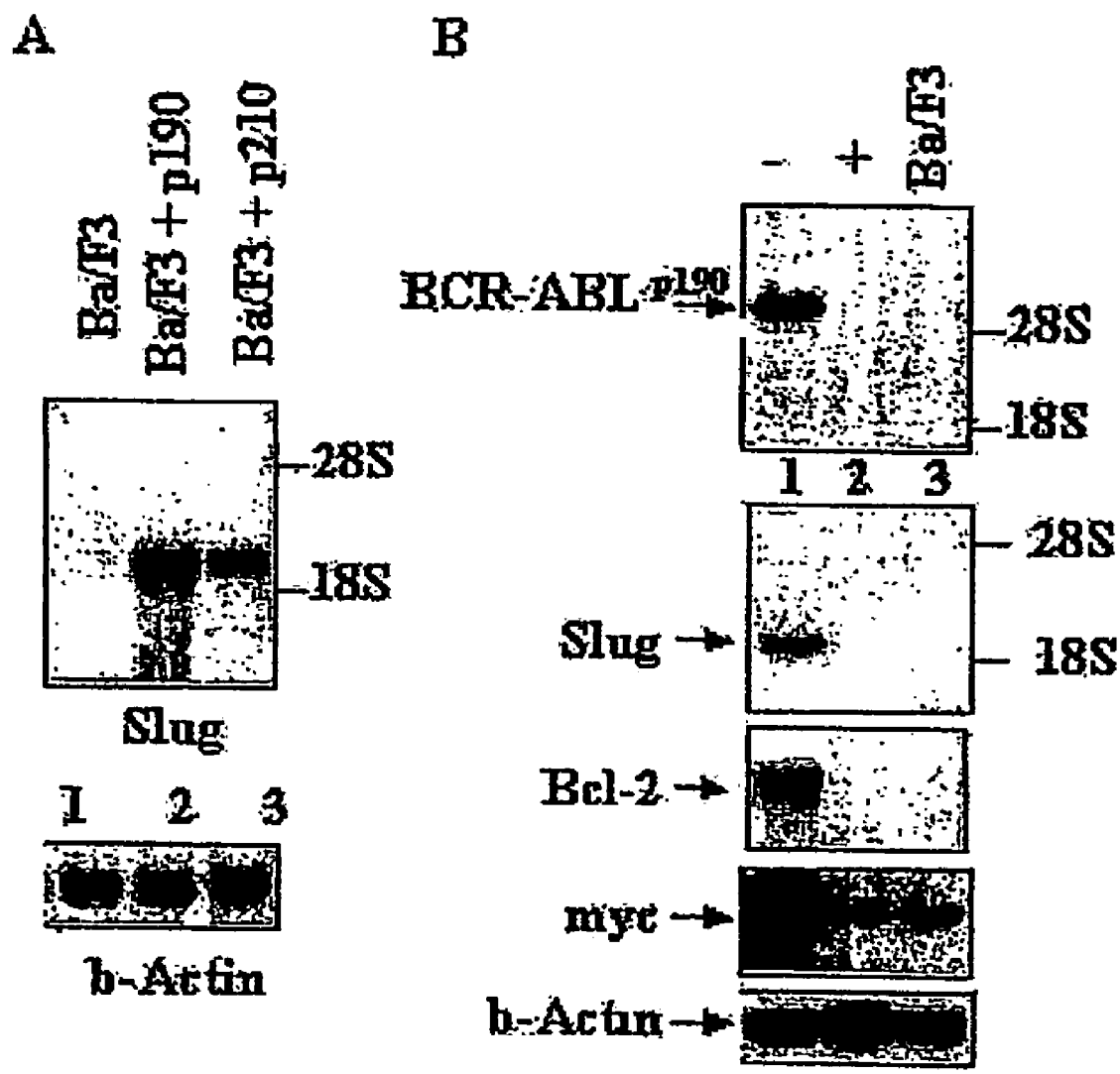
FIG. 1 illustrates the positive regulation of the Slug gene by BCR-ABL.

The invention relates, in general, to the use of the Slug gene or transcription or expression products thereof (RNA or protein) in the detection and/or treatment of cancerous cells. The Slug gene codes for a transcription factor of the "zinc fingers" type (SLUG) implicated in epithelial-mesenchymal transitions. It has now been discovered that cancerous cells, in particular, mesenchymal tumor cells, express significantly elevated levels of the Slug gene and/or transcription or expression products thereof (RNA or protein), in comparison with normal cells, which allows a method to be established for the detection of said malignant cells based on the aberrant expression of the Slug gene or transcription or expression products thereof (RNA or protein).

1. Detection of Cancerous Cells

In a first aspect, the invention provides a method for the detection of cancerous cells in a test sample, based on the evaluation of the aberrant expression of the Slug gene or transcription or expression products thereof (RNA or proteins), in comparison with the expression of said gene or transcription or expression products thereof (RNA or protein) in a control sample. This method can be applied to any vertebrate suspected of having said cells, in particular, in mammals, for example, in human beings.

The method provided by this invention is suitable for the detection of cancerous cells that express said Slug gene or transcription or expression products thereof (RNA or protein), such as mesenchymal tumor cells, for example, leukemia or sarcoma, and therefore, it is of use in the diagnosis of disease caused by said cells, as well as in the evaluation of its progression and in the determination of residual disease after treatment, essential aspects in the treatment of said disease.

In the sense used in this description, the term "test sample" refers to a biological sample of a vertebrate suspected of having mesenchymal or cancerous tumor cells.

The term "control sample," as it is used here includes (i) biological samples of vertebrates that do not have mesenchymal or cancerous tumor cells, and (ii) biological samples of vertebrates that have mesenchymal or cancerous tumor cells in order to obtain information relating to the prognosis of the disease in vertebrates that contain said cells.

By "aberrant expression," as it is used in this specification, it should be understood, in general, the altered expression of a gene or transcription or expression products thereof (RNA or protein) in cells from a tumorigenic tissue with respect to the expression of said gene or transcription or expression products thereof (RNA or protein) in normal cells of the same non-tumorigenic tissue. The aberrant expression of a gene includes the amplification of the gene, the over-expression of the gene and the expression of the gene in cells that normally do not express it.

1.A Detection Based on the Aberrant Expression of the Slug Gene

The invention provides a method for detecting the presence of cancerous cells in a test sample, based on the aberrant expression of the Slug gene, which comprises:

1) obtaining a biological sample of a vertebrate suspected of having cancerous cells, by which a test sample is obtained;

2) evaluating the expression of the Slug gene in the cells contained in said test sample; and 3) comparing the expression of the Slug gene in the cells of the test sample with the expression of the Slug gene in the cells of a control sample;

in which the presence of an aberrant expression, of the Slug gene in the cells of the test sample, when it is compared with the expression of the Slug gene in the cells of the control sample, is indicative of the presence of cancerous cells in said test sample.

In a particular embodiment, the method for the detection of cancerous cells based on the aberrant expression of the Slug gene provided by this invention is applied to a human being suspected of having said cells. The cDNA sequence of the human Slug gene as well as the amino acid sequence derived from the cDNA have been described by Nieto and others (Nieto et al., 1994, cited above).

In a particular embodiment, the cancerous cells to be detected are mesenchymal tumor cells, for example, leukemias or sarcomas.

The test sample is obtained from a biological sample of the vertebrate to be tested. Said biological sample can be obtained by any conventional method, for example, by biopsy of the tissue or blood extraction.

The aberrant expression of the Slug gene in mesenchymal or cancerous tumor cells includes amplification of the Slug gene, overexpression of said gene and expression thereof in cells that normally do not express it. Currently, it is accepted that the amplification of DNA plays a crucial role in the progression of tumors, allowing the cancerous cells to regulate numerous genes. On the other hand, the frequency of the amplification of the DNA as well as the increase in the number of copies during progression of different cancers, generally in patients who do not respond to treatment, suggests that the overexpression of the amplified target genes confers a selective advantage on the malignant cells.

The expression of the Slug gene may be evaluated by any appropriate conventional method, for example, determining the level of mRNA corresponding to the Slug gene (SLUG mRNA), or determining the number of copies of Slug gene produced.

In the sense used in this description "determining the level of SLUG mRNA" includes any method that allows qualitative or quantitative measurement or estimation of the level of mRNA that can be translated into the SLUG protein in cells of a test sample, either directly or relatively by comparing it with the level of SLUG mRNA in cells in a control sample. Similarly, "determine the number of copies of Slug gene produced" includes any method that allows qualitative or quantitative measurement of the number of copies produced of the Slug gene in cells of a test sample, either directly or relatively, by comparing it with the number of copies of the Slug gene produced in cells of a control sample. In a particular embodiment, the level of SLUG mRNA or the number of copies of the Slug gene produced in the cells of the test sample is measured or estimated and then compared with the level of SLUG mRNA or with the number of copies of the Slug gene produced in the cells of the control sample.

In a particular embodiment, the control sample can be a biological sample of a vertebrate that does not have cancerous cells, for example, mesenchymal tumor cells. In this case, once the level of SLUG mRNA or the number of copies of the Slug gene is known in the control sample, the resulting information can be used repeatedly as a standard for purposes of comparison. Alternatively, the control sample can be a biological sample of a vertebrate that has cancerous cells, for example, mesenchymal tumor cells, whereby, in this case, the level of SLUG mRNA or the number of copies of the Slug gene will provide information relating to the prognosis of the disease among vertebrates that contain said cells.

The determination of the number of copies of the Slug gene can be performed by any appropriate conventional method, for example, visualizing extrachromosomal double minutes (dmin) or integrated homogeneously staining regions (hsrs) (Gebhart et al., Breast Cancer Res. Treat. 8: 125 (1986); Dutrillaux et al., Cancer Genet. Cytogenet. 49: 203 (1990)), by means of hybridization techniques using appropriate probes obtained by conventional methods in view of the nucleotide sequence of the Slug gene, etc.

Similarly, the level of SLUG mRNA can be determined by any appropriate conventional method, for example, by Northern blot analysis (Harada et al., Cell 63: 303-312 (1990)), mapping with S1 nuclease (Fujita et al., Cell 49: 357-367 (1987)), polymerase chain reaction (PCR) (U.S. Pat. Nos.

4,683,195, U.S. Pat. No. 4,683,202, and U.S. Pat. No. 4,965, 188), retrotranscription in combination with polymerase chain reaction (RT-PCR) (Makino et al., Technique 2: 295-301 (1990)), microarray hybridization techniques (Wooster R., Trends in Genetics 16: 327-329 (2000)), etc. In a particular embodiment, the expression of Slug mRNA has been evaluated by means of Northern Blot analysis and RT-PCR (see *Materials and Methods*).

In accordance with the invention, the presence of an aberrant expression of the Slug gene in the test sample, when compared with expression of the Slug gene in the control sample, is indicative of the presence of mesenchymal or cancerous tumor cells in said test sample.

1.B Detection Based on the Expression Product of the Slug Gene

The invention also provides a method for detecting the presence of cancerous cells in a test sample, based on the expression of the expression product of the Slug gene (SLUG protein), which comprises:

a) obtaining a biological sample of a vertebrate suspected of having cancerous cells, with which a test sample is obtained;

b) evaluating the expression of the SLUG protein in cells of said test sample; and c) comparing the expression of the SLUG protein in the cells of the test sample with the expression of the SLUG protein in cells of a control sample;

in which the presence of an aberrant expression of the SLUG protein in the cells of the test sample, when compared with the expression of the SLUG protein in the cells of the control sample, is indicative of the presence of cancerous cells in same test sample.

In a particular embodiment, the cancerous cells to be detected are mesenchymal tumor cells, for example, leukemias or sarcomas.

Just as in the preceding alternative [1.A], the test sample is obtained from a biological sample of the vertebrate to test, for example, a human being, by any conventional method, for example, by biopsy of the tissue or extraction of blood.

The expression of the SLUG protein can be evaluated by any appropriate conventional method, for example, by means of techniques based on the use of antibodies, techniques based on in vivo image diagnosis, flow cytometry, proteomics, etc.

By way of example, the expression of SLUG protein in tissues can be studied by using classical histological immunological methods, in which the specific recognition is provided by an anti-SLUG antibody while the detection system can use secondary antibodies labeled with appropriate markers. The expression of the SLUG protein in a tissue can also be studied by Western Blot or dot/slot analysis (Jalkanen et al., J. Cell Biol. 101:976-985 (1985); Jalkanen et al., J. Cell Biol. 105: 3087-3096 (1987)), by immunoassays, such as ELISA (enzyme linked immunabsorbent assay) or RIA (radioimmunoassay).

In addition, the expression of the SLUG protein can be detected in vivo by means of image diagnostic techniques employing anti-SLUG antibodies bound to appropriate markers, for example, markers detectable by X-rays, nuclear magnetic resonance (NMR), etc. A review of the imaging diagnosis of tumors can be found in Tumor Imaging: The Radiochemical Detection of Cancer (S. W. Burchiel & B. A. Rhodes, eds., Masson Publishing Inc. (1982)).

Anti-SLUG antibodies that can be used in the method provided by this invention include antibodies against the intact SLUG protein or against an antigenic fragment thereof, optionally conjugated to a carrier. The antibodies can be polyclonal or, preferably, monoclonal, which can be obtained by hybridoma technology (Kohler et al., Nature 256: 495 (1975)). Alternatively, antibody fragments can be used, for example, Fab, F(ab')$_2$, etc.

Other methods for determining the expression of the SLUG protein in tissues include flow cytometry (Ward M. S., Pathology 31: 382-392 (1999), proteomics (Pandey M. & Mann M., Nature 405: 837-846 (2000); Chambers et al., J. Pathol. 192: 280-288 (2000), etc.

In accordance with the invention, the aberrant expression of the SLUG protein in cells of the test sample, when compared with the expression of the SLUG protein in cells of the control sample, is indicative of the presence of cancerous cells in said test samples.

2. Treatment of Cancer

In a second aspect, the invention relates to the use of the Slug gene or transcription or expression products thereof, in the treatment of cancer, in particular, in the treatment of pathologies related to the presence of cancerous cells, such as mesenchymal tumor cells, for example leukemia or sarcoma.

In the sense used in this description, "the use of the Slug gene or transcription or expression products thereof in the treatment of cancer" includes any method that allows qualitative or quantitative interference with the Slug gene, the level of mRNA that can be translated into the SLUG protein, or with the SLUG protein itself.

In this sense, the invention provides a pharmaceutical composition that comprises a therapeutically effective quantity of an antibody that recognizes the SLUG protein, or a fragment thereof, or a compound that interferes in the function of Slug at the DNA level, or at the RNA level, or at the protein level (SLUG), optionally along with the pharmaceutically acceptable excipients.

The anti-SLUG antibodies that can be used in the elaboration of the pharmaceutical composition provided by this invention can be antibodies against the intact SLUG protein or against an antigene fragment thereof, optionally conjugated to a carrier. The antibodies can be obtained using the hybridoma technology (Kohler et al., Nature 256: 495 (1975)). Alternatively antibody fragments can be used, for example, Fab, F(ab')$_2$, etc., which can be obtained by conventional methods.

The compound that interferes with the Slug function, both at the DNA level and at the RNA or protein level (SLUG) can be any compound, or mixture of compounds, which impede expression of the Slug gene, or which deactivate the SLUG mRNA that is generated, for example, by anti-sense oligonucleotides or ribosomes, or which deactivate the SLUG protein, for example, by use of antibodies or which compete for the effect of said protein with negative dominants (Choo, Y, et al. J. Mol. Biol. 273: 525-532, (1997); Cobaleda, C., & Sánchez-García, I., Blood 95: 731-737 (2000)).

The excipients that may be present in the pharmaceutical composition of the invention will depend, among other things, on the administration route of said pharmaceutical composition. A review of the different administration routes of active substances, the excipients to use and their manufacturing processes can be found in the Treatise on Formulation Pharmacy, C. Fauli i Trillo, Luzán 5, S. A. of Editors, 1993.

The invention also relates to a method for in vitro screening of antitumoral agents based on the regulation of the expression of the Slug gene that comprises (i) developing a cellular system that, in certain conditions, expresses the Slug gene, (ii) bringing said cell system into contact with the compound to be tested, and (iii) evaluating the expression of the Slug gene, such that if the Slug gene is not expressed, the compound tested is a potential antitumoral agent.

Interference with the function of the Slug gene can be performed at the DNA level by impeding its expression, deactivating the mRNA that is generated by antisense oligonucleotides or ribosomes, deactivating the protein by using antibodies or competing with the effect of said protein with negative dominants (Choo, Y, et al. J. Mol. Biol. 273: 525-532, (1997); Cobaleda, C., & Sánchez-García, I., Blood 95: 731-737 (2000)).

The invention will now be illustrated by means of an assay performed by the inventors, which shows that the Slug gene regulates the disseminative capacity of the leukemia cells with BCR-ABL.

I. Materials and Methods

Cell Cultures

The cell lines used include BalF3 cells (Palacios and Steinmetz, Cell 41: 727 (1985)) and Ba/F3 cells that express the human proteins BCR-ABLP$^{190}$ (Ba/F3+p190) and BCR-ABLP$^{210}$ (Ba/F3+p210) (Sánchez-García and Grütz, Proc. Natl. Acad. Sci. USA, 92: 5287-5291 (1995)). The cells were maintained in Dulbecco modified Eagle medium (DMEM) supplemented with 10% fetal calf serum (FCS). When it was necessary, 10% of medium was added conditioned with WEHI-3B as source of IL-3 (interleukin-3).

Representational Difference Analysis

The RDA was performed as described by Hubank and Schatz (Hubank and Schatz, Nucleic Acid Res. 22: 5640-5648 (1994)). In summary, mRNA was isolated from Ba/F3, Ba/F3+p190 and Ba/F3+p210 cells. A sample of 10 mg of mRNA was extracted from each cell population for the RDA. cDNA was synthesized from the mRNA and digested with Dpn II. Adaptors were added to the cDNA digested with Dpn II composed of two oligonucleotides: (R-24) [SEQ ID NO: 1] and (R-12) [SEQ ID NO: 2]. The resulting mixture was amplified by PCR with R-24 oligonucleotides [SEQ ID NO: 1] and the adaptors were cleaved with Dpn II. Then, a second pair of adaptors were bound: (J-24) [SEQ ID NO: 3] and (J-12) [SEQ ID NO: 4] to the amplified fragments from the Ba/F3+p190 and Ba/F3+p210 (tester) cells. These were then hybridized with the amplified cDNA fragments with R-24 [SEQ ID NO: 1] from Ba/F3 cells (inductor) with a ratio of 1:100 for 20 hours. The hybridization mixture was used as a template for the PCR based amplification.

A second round of removal was performed by withdrawing the J adaptors [SEQ ID NO: 3 and SEQ ID NO: 4] from an aliquot of the product of the first round of PCR, binding a third pair of oligonucleotide adaptors: (N-24) [SEQ ID NO: 5] and (N-12) [SEQ ID NO: 6] and hybridising with induction amplicons at a ratio of 1:1000. The PCR products were separated on 2.0% agarose gel and the individual bands subcloned and examined by Northern Blot Analysis with respect to the differential expression.

Retrotranscription Polymerase Chain Reaction (RT-PCR)

In order to analyse the expression of SLUG in human cell lines and in peripheral blood samples in patients positive for Ph-1, an RT was performed in accordance with the manufacturer's protocol in a reaction of 20 µl that contained 50 ng of random hexamers, 3 µg of total RNA and 200 units of Superscript II RNAse H$^{31}$ reverse transcriptase (GIBCO/BRL). The parameters of the thermal cycles for the PCR and the sequences of the specific primers were as follows: SLUG, 30 cycles at 94° C. for 1 minute, 56° C. for 1 minute and 72° C. for 2 minutes, primer in correct sense [SEQ ID NO: 7] and antisense primer [SEQ ID NO: 8]; c-ABL, 30 cycles at 94° C. for 1 minute, 56° C. for 1 minute and 72° C. for 2 minutes with the correct sense [SEQ ID NO: 9] and antisense primer [SEQ ID NO: 10]. The amplification of the mRNA of c-ABL served as a control to evaluate the quality of each sample of RNA. The sequences of the internal probes were the following:
SLUG: SEQ ID NO: 11, and
c-ABL: SEC. ID. NO. 12.

Cloning of cDNA of Slug of Complete Length by RT-PCR

The Slug cDNA of mouse was cloned by RT-PCR using the advance primer (SEQ ID NO: 13) and the reverse primer (SEQ ID NO: 14) (GenBank accession number U70550).

Analysis of the RNA

The total cytoplasmic RNA (10 µg) was glyoxylated and fractioned on gels with 1.4% agarose in 10 mM Na$_2$HPO$_4$ buffer (pH 7.0). After electrophoresis, the gel was transferred to Hybond-N nylon membranes (Amersham), which were treated with UV light and hybridized with probes labeled with $^{32}$P. The charge was controlled, re-treating the filters with a cDNA probe of β-actin. The antisense Slugh oligonucleotide used as a probe comprises the first 34 bases of the sequence coding for the Slugh cDNA of mouse.

Plasmid Construct for In Vivo Studies

The Slug cDNA of mouse was amplified by PCR to facilitate cloning by adding restriction enzymes, using primers that hybridize with the 5' and 3' terminals of cDNA and amplifying a region that included the entire coding region of the gene. The Slugh cDNA of mouse was cloned both in the sense and antisense orientation in the pEF-BOS vector (denominated BOS-Slug and BOS-antiSlug, respectively), which contained sequences of the EF1-α promoter followed by a region of polyengarce bound to the signal of poly(A)adenylation of the cDNA of human G-CSF, as has been described (Mizushima and Nagata, Nucleic Acid Res. 18: 4322 (1990)). The Combi-p190 vector was obtained by replacing the cDNA of the luciferase of the Combi-tTA plasmid (Schultze et al., Nature Biotechnology 14: 499-503 (1996)) with the cDNA of BCR-ABLP$^{190}$. The authenticity of the constructs was confirmed by DNA sequencing.

Cellular Transfection

Ba/F3 cells were transfected by electroporation (960 µF, 220 V) with 20 µg of Combi-p190, respectively, along with 1 µg of MC1-neo expression vector. In the cells (Ba/F3+combi p190), the expression of BCR-ABL was analyzed by Northern Blot in the presence and in absence of tetracycline (20 ng/ml). These cells were resistant to the absence of IL-3 when they were developed in the presence of tetracycline.

Expression of the Murine Slug Gene in Cells that Express Ba/F3 and BCR-ABL and Cell Survival Assay Ba/F3, Ba/F3+p190 and Ba/F3+p210 cells were transfected by electroporation (960 µF, 220 V) with 20 µg of BOS-Slug and BOS-antiSlug, respectively, along with 1 µg of pure MCl expression vector. In the cell lines, Slug expression was analyzed by Northern blot. The cells were selected with respect to the resistance to the absence of IL-3 and cell viability was determined by exclusion with trypan blue.

DNA Analysis

The low-molecular weight DNA was isolated as indicated below. The cells were collected in 1.5 ml of culture medium, micro-centrifuged for 1 minute at 1500 rpm (400×g) and the sediments suspended in 300 µl of proteinase K buffer. After an incubation period of one night at 55° C., the DNA was precipitated with ethanol, suspended in 200 µl of TE buffer that contained 50 µl/ml of RNAse A and incubated at 37° C. for 2 h. The DNA was extracted with phenol and chloroform and precipitated with ethanol. DNA aliquots (2 µg) were labeled at the termini with α32-dCTP and submitted to electrophoresis on 2% agarose gel. After electrophoresis, the gel was transferred to a Hybond N (Amersham) and autoradiographed for 2hat-70° C.

Phenotype Analysis

For the cytometry staining, the following monoclonal anti-mouse antibodies from Pharmingen were used: the lymphoid marker CD45R/B220 and the myeloid marker Gr-1. Suspension of a single cell of the different cell lines obtained by routine techniques with anti-mouse CD32/CD16 (Pharmingen), purified to block binding by Fc receptors, were incubated with an appropriate dilution of different antibodies at room temperature or at 4° C., respectively. The samples were washed twice with PBS and re-suspended in PBS. Dead cells were excluded by staining with propidium iodide. The samples and the data were analyzed by FACScan using the CellQuest software (Becton Dickinson).

Tumorigenicity Assay

In order to assay the tumorigenicity of the different cell lines, $10^6$ cells re-suspended in 200 µl of saline solution buffered with phosphate were injected subcutaneously into both sides of male athymic (naked) mice aged 2 to 4 weeks old. The formation of tumors in the animals was examined during the course of two months.

Histological Analysis

The tumor samples were fixed in 10% formaline overnight. They were then processed and set in paraffin blocks. Sections of 6 µm were stained with haematoxylin and eosin, examined histologically and photographed. All the sections were taken from homogeneous and viable portions of the tumors submitted for dissection.

II. Results

BCR-ABL Positively Regulates the Expression of Slug in Haematopoietic Cells

Molecular characterization of certain chromosomal abnormalities associated with cancer in humans has shown that the main consequences are tumor-specific fusion proteins.

A common idea put forward is that the creation of these proteins alters the normal development of the tumor-specific target cells blocking apoptosis (Cobaleda et al., BioAssays 20; 922 (1998)), but the most threatening aspects for life due to the oncogenic process are invasion and metastasis. Although the clinical significance of such expression of the malignant phenotype has been correctly appreciated, the lack of understanding of the molecular mechanisms implicated in the invasion have delayed other development work in the field of cancer research. Thus, an initial critical stage for understanding the malignant transformation mediated by the products of the chromosomal abnormalities associated with leukemia is the identification of reporter genes downstream from those that direct these proteins. The BCR-ABL oncogenes are being used as an experimental model and benefit has been obtained from a cell system that uses a murine haematopoietic precursor Ba/F3 cell line transduced with vectors that code for the BCR-ABL fusion protein (Sánchez-García and Grütz, 1995, cited earlier). The expression of BCR-ABL in Ba/F3 induces cell transformation, confers an independent growth of cytokines and blocks apoptosis (Daley and Baltimore, Proc. Natl. Acad. Sci. USA 85: 9312 (1988); Sánchez-García and Grütz, 1995, cited earlier). In order to identify potential targets for the action of BCR-ABL, a substrate process has been chosen for the representational difference analysis (RDA). Using mRNA molecules from Ba/F3 cells, and Ba/F3 cells that expressed BCR-ABLp190 (Ba/F3+p190) and Ba/F3 cells that expressed BCR-ABLp210 (Ba/F3+p210), cDNA was prepared and submitted to three cycles of sequential hybridization and PCR amplification in accordance with the RDA protocol of Hubank and Schatz (Hubank and Schatz, 1994, cited earlier). Several fragments of differentially amplified cDNA fragments were individually subcloned and assayed with respect to differential gene expression by Northern Blot analysis of Ba/F3 RNA. A fragment of cDNA was identified that represented a gene regulated differentially and denoted I-1. Comparison of sequences showed that the 527 nucleotide I-1 fragment corresponded to a part of the coding region and the untranslated 3' region of murine SLUG cDNA (Nieto et al, 1994, cited earlier), identified with the BLAST search utility (National Center for Biotechnology Information).

The capacity of the BCR-ABL oncogenes to stimulate production of SLUG mRNA was assayed by hybridization with Northern mRNA Ba/F3, Ba/F3+p190 and Ba/F3+p210 cell filters (FIG. 1A). Northern blot analysis showed the expression of SLUG in Ba/F3+p190 and Ba/F3+p210 cells. This assay shows that the cells positive for BCR-ABL express SLUG mRNA, but that the control cells do not. Therefore, these data indicate a clear relationship between activation of the Slug gene and the expression of BCR-ABL in this system.

The Presence of BR-ABL is Required for Aberrant Expression of SLUG

The data described above show the aberrant expression of SLUG I cells that contain the fusion gene BCR-ABL. In order to determine whether BCR-ABL is required for transcription of the Slug gene, Ba/F3 cells were created in which expression of the BCR-ABL gene could be exogenously regulated. The Combi-tTa system was used, which has the transactivator and minimum promoter of the tet operator that directs the gene expression unit in a single plasmid (Schultze et al., 1996, cited above). The repressor tet protein fused to the transactivator domain of viral VP 16 was bound, in the absence of tetracycline, to a minimum promoter of the tet operator obtained by genetic engineering and activated the transcription of BCR-ABL (Combi-p190). In the presence of the effecter molecule, the binding was cancelled and the promoter silenced (FIG. 1B). In this sense, although BCR-ABLP[190] was detected in Ba/F3+Combip190 without tetracycline, mRNA was not found in the presence of tetracycline (20 ng/ml). These data indicate that the induction of BCR-ABL can be completely suppressed by tetracycline.

The specificity of the activation of the Slug gene was analyzed by Northern hybridization of Northern filters in Ba/F3+Combip190 cells. After two days of culturing, in the presence or absence of tetracycline, SLUG expression was determined. As shown in FIG. 1B, SLUG expression was rapidly reduced, coinciding with the reduction of the expression of mRNA of BCR-ABLPp190. In addition, in these cells, it was analyzed whether the expression of two well-known downstream effectors of the BCR-ABL oncogenes, Myc (Sawyers et al., Cell 70: 901-910 (1992)) and Bcl-2 (Sánchez-García and Grütz, 1995 cited above; Sánchez-García and Martín-Zanca, J. Mol. Biol. 267: 225 (1997)) were dependent on the presence of BCR-ABL. As shown in FIG. 1B, although expression of both Bcl2 and Myc was detected in Ba/F3+Combip190 without tetracycline, no mRNA could be found in presence of tetracycline (FIG. 1B). This observation confirms that the changes observed in the gene expression were stimulated by NCR-ABL.

Figure 2:
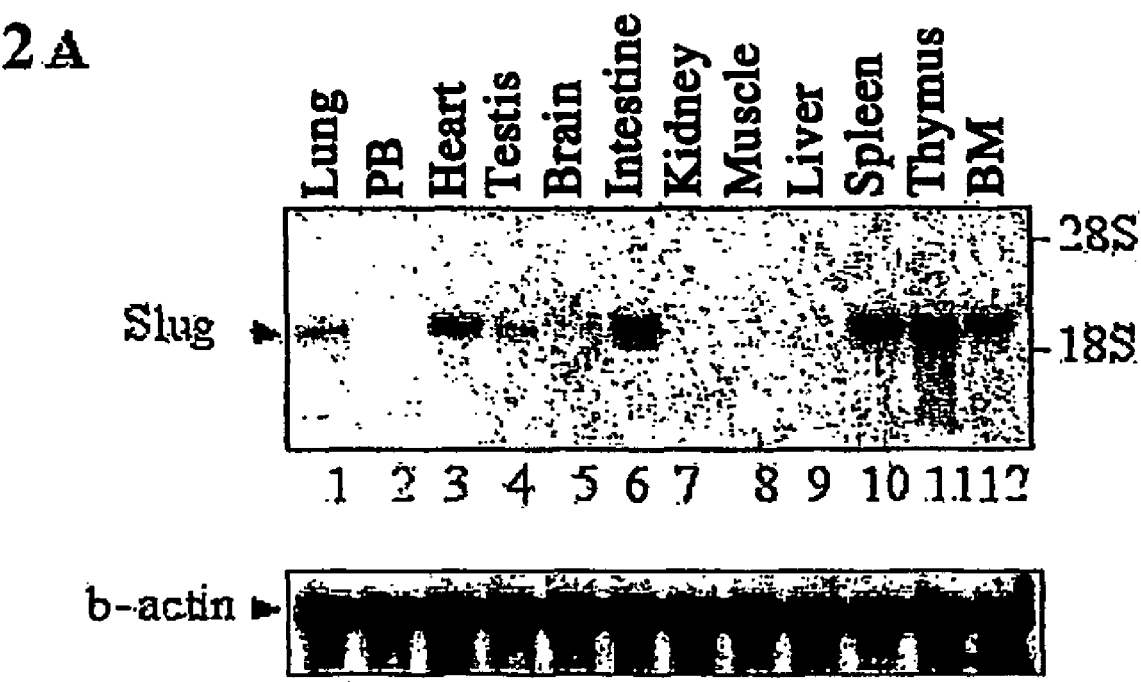
FIG. 2 shows the expression of SLUG mRNA in tissues of normal mice.
Figure 2:
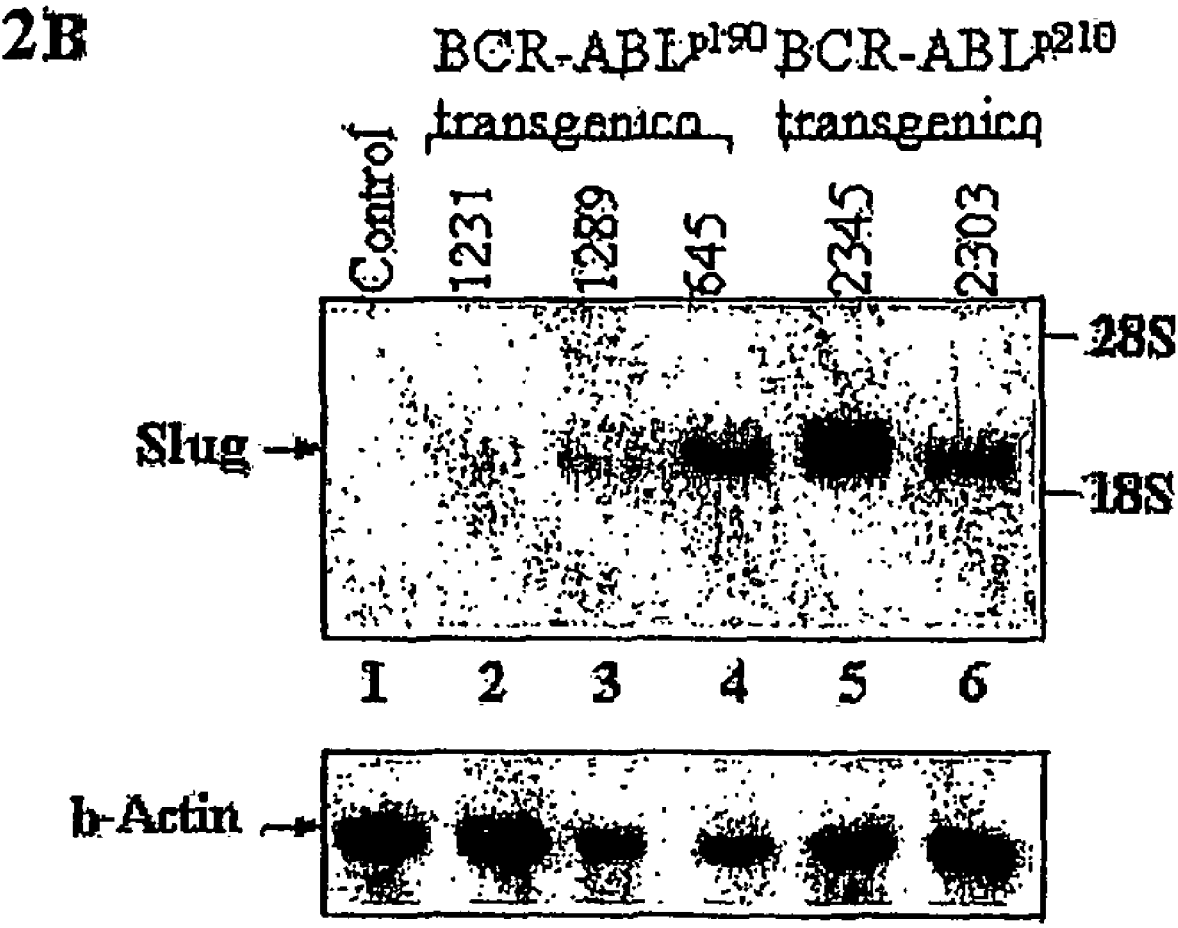
Figure 3:
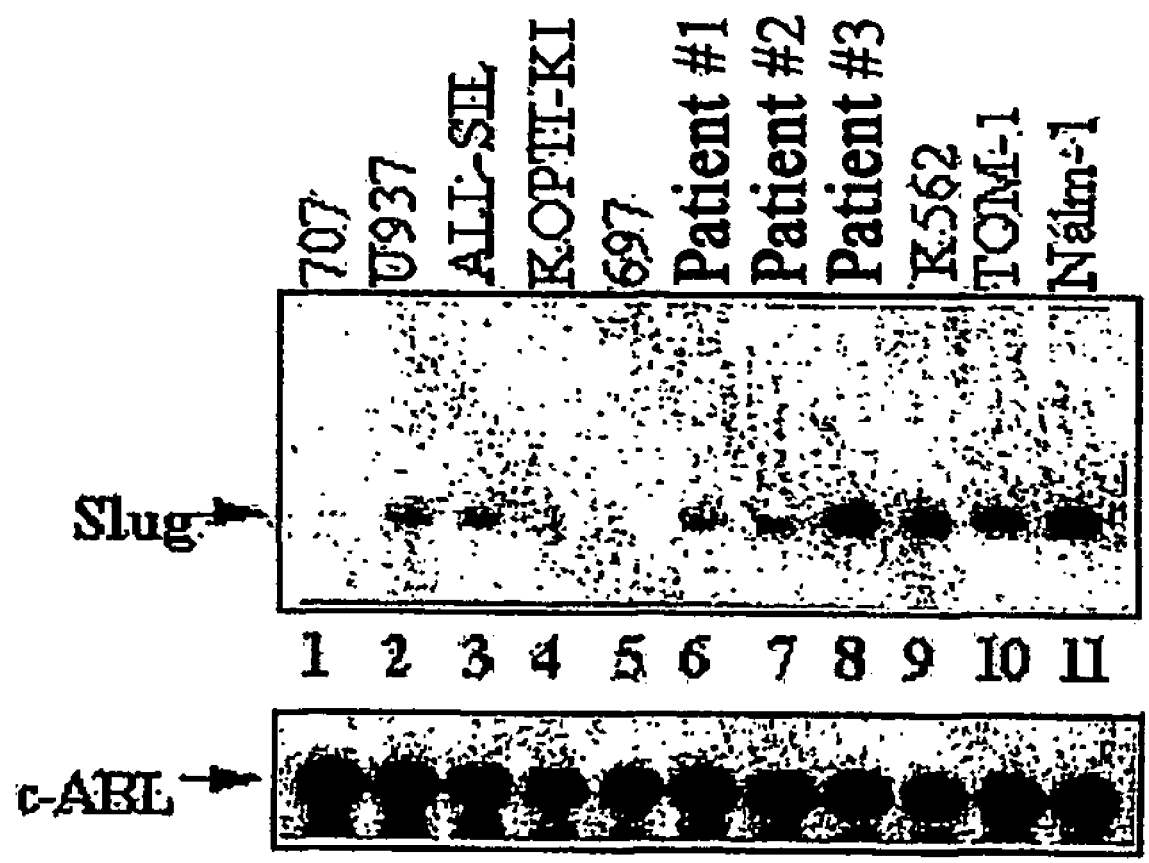
FIG. 3 illustrates that the endogenous SLUG is present in human invasive cell lines. Each RNA molecule is transcribed by means of retrotranscription (RT) and the PCR products are transferred to a nylon membrane and analyzed by hybridization with internal oligonucleotide probes labeled specifically at the terminus for each gene. The RNA were evaluated for the non-leukemia haematopoietic cell line 707 (band 1), for the myeloid leukemia cells U937 (band 2), for ALL-SIL leukemia T cell lines (band 3) and KOPTI-KI (band 4), for the pre-B leukemia 697 cell lines (band 5), for samples of patients with t(9;22) (bands 6 to 8) and for human leukemia cell lines positive for t(9;22) K562 (band 9), TOM-1 (band 190) and Nalm-1 (band 11).

Slug Expression is Present in Cell Lines and Peripheral Blood Cells of Patients with Leukemia Positive for the Philadelphia Chromosome The discovery that BCR-ABL positively regulates expression of Slug in Ba/F3 cells led the inventors to test whether the levels of expression of Slug are also positively regulated as a consequence of expression of BCR-ABL in primary parent cells, the natural target of the oncogenic BCR-ABL fusion protein (Cobaleda et al., 2000; Sánchez-García, 2000, cited above). Northern blot analysis of a spectrum of mouse tissue indicated that, with rare exceptions, SLUG is widely expressed in mouse tissue (FIG. 2A). However, SLUG is not expressed by the peripheral blood leukocytes (FIG. 2A). Knowing that SLUG is not expressed in peripheral blood of normal mice, the possible effects of expression of BCR-ABL on the levels of SLUG mRNA in peripheral blood of transgenic BCR-ABL mice with leukemia were tested (Castellanos et al., Blood 90: 2168 (1997)). The parent cells of mouse that expressed BCR-ABL by hybridization with Northern filters were examined (FIG. 2B). Each band of RNA was evaluated with respect to integrity and charge by hybridization with a probe of β-actin (FIG. 2B, lower section). In accordance with the results observed in Ba/F3 cells, the primitive cells with BCR-ABL produced an increase in the expression of SLUG Afterwards, it was tested whether the expression of SLUG was also present in primitive cells of patients with human leukemias positive for Ph1. It was shown that the expression product of the Slug gene was absent in cells from normal human samples (FIG. 3, band 1). On the contrary, the expression of SLUG was present in cells of patients with the Philadelphia chromosome (FIG. 3, bands 6-8). The cell lines K562, Nalm-1 and TOM-1, positive for t(9; 22), come from patients with LMC and from LLA patients positive for Ph1. Therefore, these cell lines were compared with a human non-leukaemic cell line with respect to expression of SLUG Examination of the mRNA for expression of SLUG by reverse transcriptase PCR showed that Slug is present in all these cell lines positive for Ph1 (FIG. 3, bands 9-11). The discovery that expression of SLUG is present in cells after expression of transformation BCR-ABL, along with the discovery that the Slug gene is present in cell lines and in bone marrow cells isolated from patients with leukemia positive for BCR-ABL, suggests that the presence of the Slug gene could be a component in the invasion of leukemias positive for BCR-ABL.

Slug is Present in Cell Lines of Leukemia Patients with Other Chromosomal Abnormalities As SLUG is a member of the Snail family of proteins implicated in the formation of the mesoderm (Nieto et al., 1994, cited above) and its expression is somewhat uncontrolled (FIG. 2), the expression of the Slug gene was then analyzed in other mesenchymal tumors. FIG. 3 shows examples of RNA from a further four leukemia cell lines that lack t(9; 22), including the lineage B primitive 697 (FIG. 3, band 5), the myeloid U937 (FIG. 3, band 3) and KOPTI-KI (FIG. 2, band 4). As shown in FIG. 3, in all leukemia cell lines, expression of the Slug gene was shown. In this sense, recent discoveries show that SLUG is also expressed in t(17; 19) leukemia cells (Inukai et al., Molecular Cell 4: 343-352 (1999)) and in radbomyosarcoma cells that express the PAX3-FKHR translocation (Khan et al., Proc. Natl. Acad. Sci. USA 96: 13264-13269 (1999)). Thus, these results combined indicate that expression of Slug is not rare in mesenchymal tumors (both leukemia or sarcoma) transformed under the auspices of other genetic alterations and suggest that the Slug gene could be a component of the biology of cancer, not only in leukemias positive for BCR-ABL, but possibly also in other mesenchymal cancers.

Antiapoptotic Activity of SLUG

Figure 4:
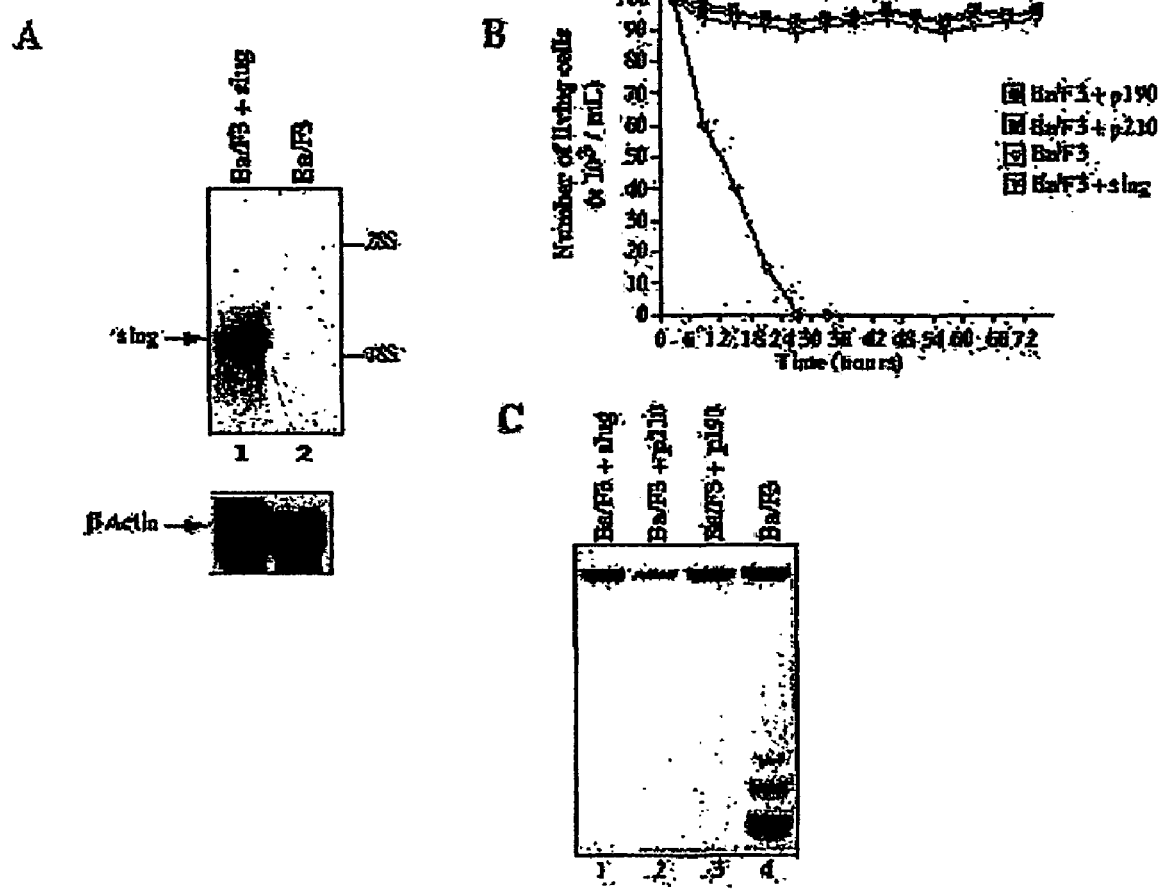
FIG. 4 illustrates the effect of the Slug gene on the survival of Ba/F3 cells in absence of growth factor.

In order to understand better the function of SLUG in the biology of cancer, the Ba/F3 cell lines transduced with vectors that code for the BCR-ABL fusion protein were also used (Sánchez-García and Grütz, 1995, cited above). The expression of BCR-ABL in Ba/F3 confers a growth independent of cytokines and blocks apoptosis (Daley and Baltimore, 1988; Sánchez-García and Grütz, 1995, cited above). Thus, the inventors were asked whether SLUG could perform these functions in the absence of the oncoprotein. Therefore, Ba/F3 cells were transfected with a vector that expressed Slug (FIG. 4A) and the cell viability was analyzed in absence of IL-3. As shown in FIG. 4, the Ba/F3 cells that expressed the BCR-ABL oncogenes survived with little loss of viability and those that expressed Slug did not undergo apoptosis after elimination of IL-3 from the growth medium (FIGS. 4B, 4C). This observation confirms the previous results (Inukai et al., 1999, cited above) and indicates that Slug blocks apoptosis in the test cell system. Thus, its deregulation by BCR-ABL in Ph$^+$ cells probably contributes to the properties of prolonged survival of the t(9; 22) cells. The Slug gene could replace BCR-ABL in the promotion of the survival of murine Ba/F3 cells deprived of growth factor, which suggests that it is more probable that it is implicated in the resistance to cell death characteristic of Ph$^+$ leukemias and a key stage towards the development of leukemias positive for t(9; 22).

Figure 5:
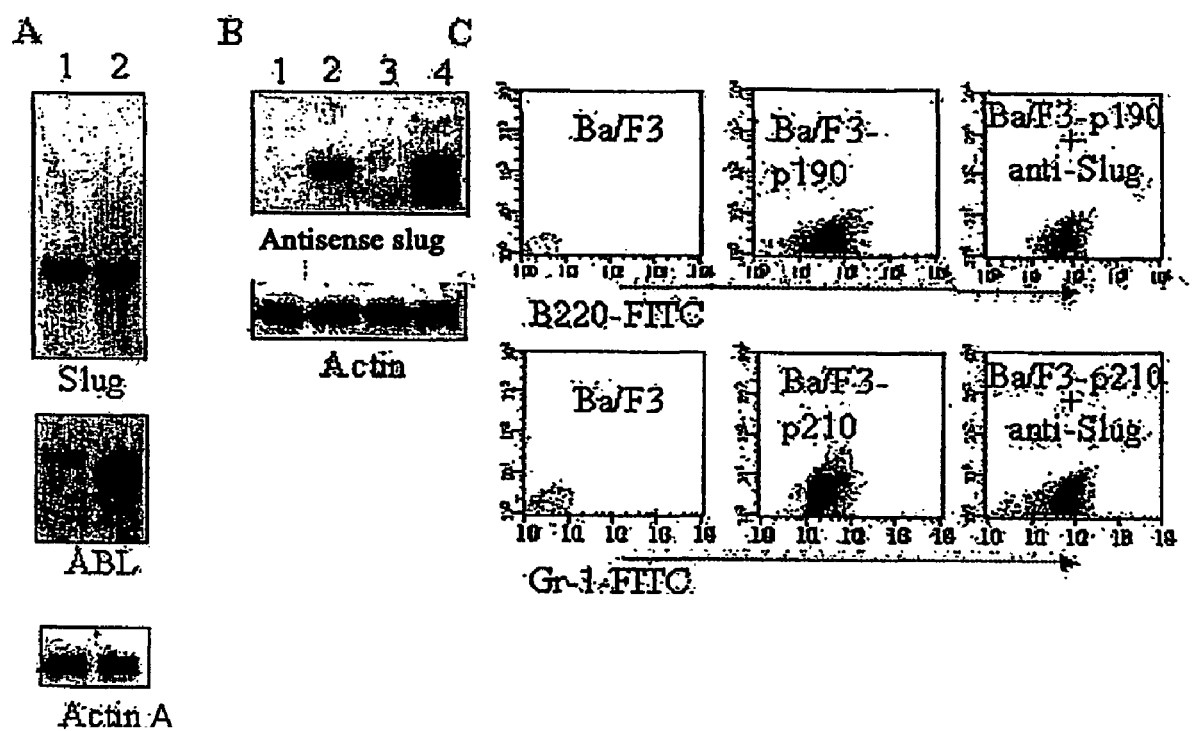
FIG. 5 illustrates the repression of SLUG mRNA in Ba/F3 cells that express BCR-ABL with antisense cDNA versus SLUG

Suppression of the Slug Gene Compromises the Tumorigenicity of BCR-ABL Oncogenes Affecting the Capacity for Dissemination of BCR-ABL Leukemia Cells The previous results show that expression of BCR-ABL protects the cells from apoptosis, inducing the Slug gene. In this case, it would be expected that some modification would be produced in the growth and tumorigenicity of the Ba/F3 cells that express BCR-ABL when the level of expression of Slug is altered. Ba/F3 cells that expressed BCR-ABL were transfected with a vector that expressed cDNA of antisense mouse Slugh (BOS-antiSlug) and clones were established (FIG. 5A). The RNA was extracted and the levels of mRNA of Slugh were compared with those present in the untransfected control cells (FIG. 5B). In cells transfected with BOS-anti-Slug, antisense Slugh was detected and in the Ba/F3 cells that expressed BCR-ABL transfected with BOS-antiSlug the level of BCR-ABL was not affected (FIG. 5A). On the other hand, SLUG mRNA was not detected in cells transfected with antisense Slugh, although it was present in Ba/F3-p190 and Ba/F3-p210 cells (FIG. 5B). The consequences of the suppression of Slugh expression were evaluated by examining the differentiation program imposed by BCR-ABL oncogenes in Ba/F3 cells and the in vivo tumorigenicity of the different cell lines by injection into naked mice.

In order to determine whether Slug expression is a critical component per se in the differentiation program induced by the BCR-ABL oncogenes, the inventors then measured the capacity to differentiate haematopoietic precursors that expressed BCR-ABL transfected in those in which expression of Slug had been specifically suppressed. The effects of the suppression of Slugh expression on cell differentiation in Ba/F3 cells that expressed BCR-ABL were evaluated by analysing the expression of specific haematopoietic markers in the different cell lines. As shown in FIG. 5C, the initial Ba/F3 cells that express BCR-ABL-p190 or BCR-ABL-p210 oncogenes are specifically differentiated in myeloid and lymphoid cells, as defined by the presence of the myeloid marker Gr-1 or the lymphoid marker B220, respectively. By analogy, differentiation of Ba/F3 cells that expressed BCR-ABL in those that expression of Slug had been specifically suppressed was not affected (FIG. 5C). These results show that the effect of the BCR-ABL oncogenes on the differentiation does not depend on the expression of Slug.

Figure 6:
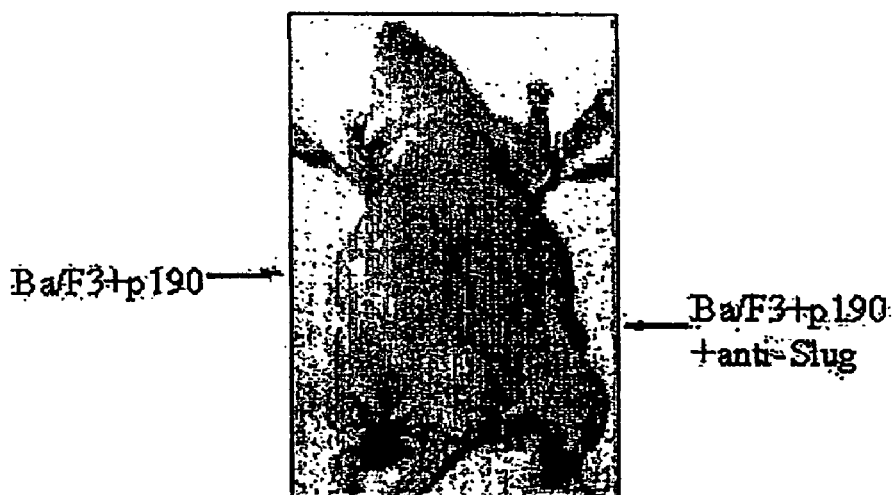
FIG. 6 shows the requirements of Slug in the tumorigenicity of Ba/F3 cells that express BCR-ABL. The initial Ba/F3 cells that expressed BCR-ABL oncogenes grew as tumors in naked mice (REF). By analogy, it was discovered that the formation of tumors was already observed at five days after injections of the cell lines that expressed BCR-ABL. In contrast to these controls, the Ba/F3 cells that expressed BCR-ABL and antisense Slug are much less tumorigenic. The tumors were sliced to perform a macroscopic analysis on day 20 after cell injection. On average, the weight of the tumors found in the mice that had been injected with Ba/F3 cells that expressed BCR-ABL were twice as high as that of the tumors induced by cells that expressed BCR-ABL and the antisense Slug construct.
Figure 7:
FIG. 7 illustrates the effect of Slug on the development of tumors by BCR-ABL cells.
Figure 7:
Figure 7:
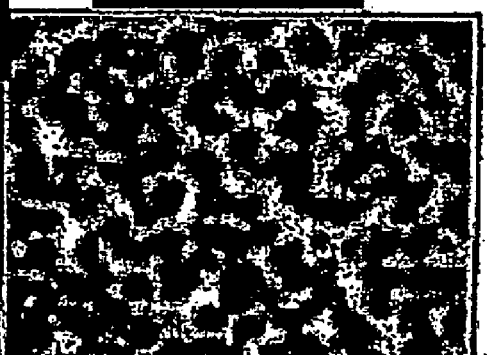

Later, the present investigators examined the in vivo tumorigenic capacity of the different cell lines. The initial Ba/F3 cells that expressed the BCR-ABL oncogenes grew as tumors in naked mice (Sánchez-García and Grütz, 1995, cited earlier). By analogy, it was described that the formation of tumors was observed just five days after injection of the cell lines that expressed BCR-ABL. In contrast to these controls, the Ba/F3 cells that expressed BCR-ABL and antisense Slugh were much less tumorigenic (FIG. 6). The tumors were cleaved to perform the macroscopic analysis on day 20 after injection of the cells. On average, the weight of the tumors found in mice that had been injected with Ba/F3 cells that expressed BCR-ABL was twice as large as the weight of tumors of mice that had been injected with cells that expressed BCR-ABL and the antisense Slugh construct (FIG. 6). During the development of the in vivo invasive tumors, the tumor cells disobeyed the social order of the boundaries of the organs and penetrated foreign tissues. Thus, later, a histological examination was performed of the BCR-ABL tumors generated in presence or absence of Slug. In the tumors originating as a result of Ba/F3 cells that expressed BCR-ABL in which the expression of Slugh had been suppressed, the cells accumulated, but the proliferation was systematically limited to the permissive medium (FIG. 7). In contrast, in tumors generated as a result of Ba/F3 cells that expressed BCR-ABL in which the expression of Slug had been modified, the previously established limits of the permissive medium extended and, thus, the tumor progressed. As shown in FIG. 7, Slug clearly confers a metastatic behavior on the BCR-ABL cells, allowing the migration of tumor cells as individual cells. Similar results were found in multiple sections of tumors and for the two forms (p190 and p210) of the BCR-ABL oncogene. Thus, these results show that the Slug gene plays a fundamental role in the transition of a tumor from in situ to invasive, allowing the migration of tumor cells as individual cells.

III. Discussion

SLUG Regulates the Invasive Capacity of BCR-ABL Cells: Consequences for the Pathogenesis of Mesenchymal Tumors In leukeamogenesis, the future tumor cells are primitive parent cells in which differentiation is blocked (Cobaleda et al., 2000; Sánchez-García, 2000, cited earlier), but the inhibition of the differentiation is not sufficient for transformation because the survival and proliferation of the target cells is restricted to a particular micro-environment. Thus, the transformation must depend on genetic changes that allow the cells to develop outside their normal environment in addition to mutations that block differentiation. In order to validate this hypothesis, it was attempted to identify the target downstream of the genes BCR-ABL fused by t(9; 22) (q34; q11) in the haematopoietic cells. Identification of the gene products downstream that confer the neoplasic nature is prerequisite for full understanding of the mechanism of leukemogenesis. In the present study, the Slug gene has been identified as a downstream target gene implicated in the leukemogenic process induced by the chimeric BCR-ABL fusion gene. The studies of the present investigators do not establish whether the Slug promoter is a direct target of BCR-ABL or whether it is more likely that this gene is implicated as an element in certain biochemical cascades that respond to modulation by the chimeric protein. The discovery that expression of Slug is present in cells after expression of transforming BCR-ABL, along with the discovery that Slug is present in cell lines and in bone marrow cells isolated from patients with leukemias positive for BCR-ABL, indicate that the presence of Slug has to be an important component of the malignant nature of the leukemias positive with respect to BCR-ABL. This suggests the possibility the Slug can contribute to blocking differentiation or can be responsible for the disseminative capacity of this disease.

Other discoveries of the inventors define the biological function of Slug in the context of cell transformation dependent on BCR-ABL oncogenes. The data presented here show that Slug, which is activated by expression of BCR-ABL oncogenes, mediates the prevention of apoptosis in the Ba/F3 system. In addition, a modification of the growth and tumorigenicity of the cells that express BCR-ABL is produced, altering the level of expression of Slug. In in vivo tumors originating as a result of BCR-ABL cells in which expression of Slug had been eliminated previously, the cells accumulated, but the proliferation was limited systematically to the permissive environment. In contrast, in tumors generated as a result of BCR-ABL cells in which expression of Slug had not been previously modified, the previous boundaries of the permissive environment spread and, as a result, the tumor progresses, disobeying the order of boundaries and infiltrating foreign tissue. Thus, Slug clearly confers metastatic behavior on the BCR-ABL cells in transition from in situ to invasive, allowing the migration of tumor cells as individual cells.

Figure 8:
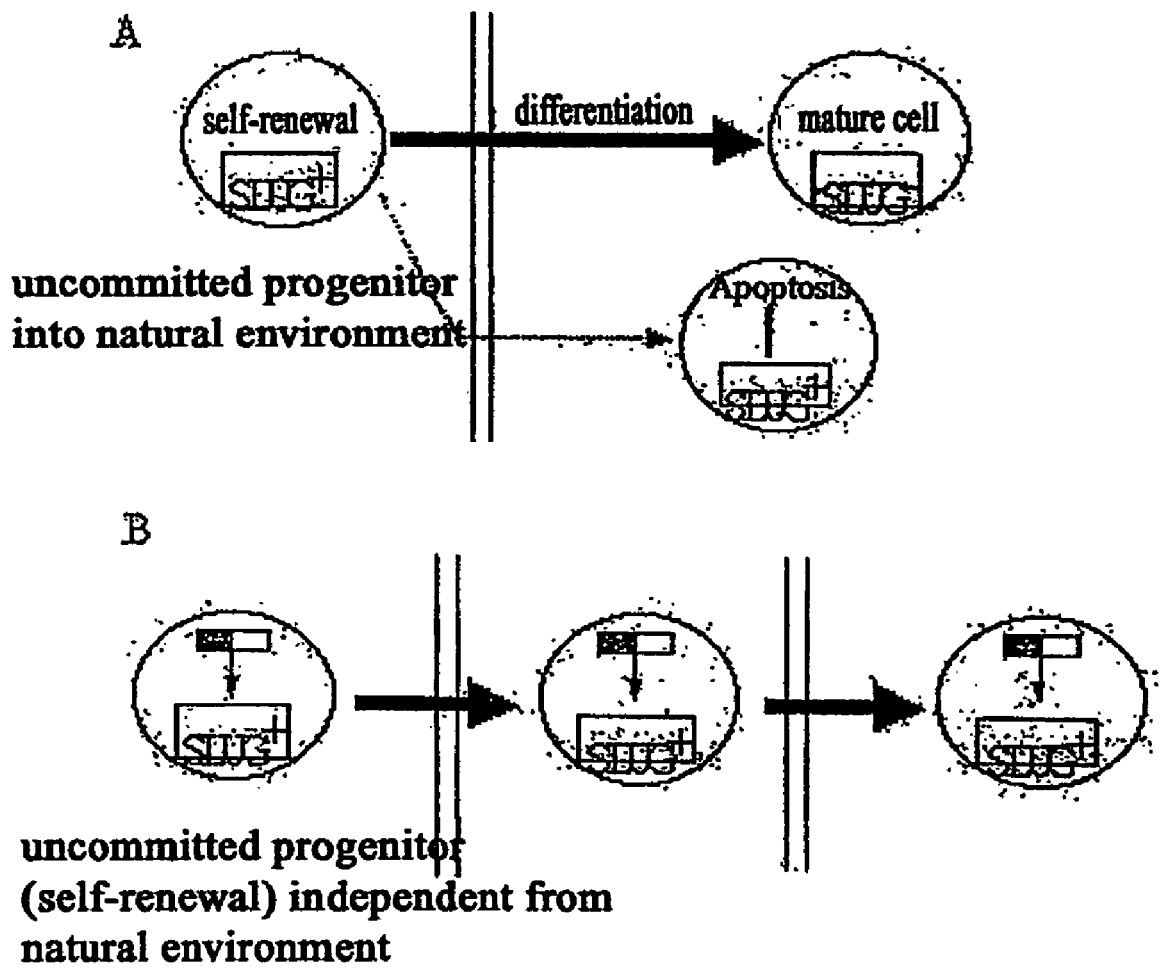
FIG. 8 is a representation that illustrates the model of the role of Slug in the development of cancer.

The discoveries of the inventors are consistent with a model in which the parent cells that carry the fusion protein BCR-ABL would constitutively express Slug, promoting both the aberrant survival of the tumoral target cell, regardless of the external signals required, which allows the cell to grow outside its normal environment, and migration of defective target cells into different environments (FIG. 8). However, an increase in expression of Slug cannot be the only event implicated in the transformation by BCR-ABL oncogenes. The reason is as follows: although the expression of constitutive Slug replaces the signals of survival induced through growth receptors and allows the cells to grow outside their normal micro-environment, the results of the present investigators show that the effect of the BCR-ABL oncogenes on differentiation does not depend on the expression of Slug. Thus, other components are required in addition to Slug in order to reconstitute the BCR-ABL transformation signal.

The inventors have shown that the BCR-ABL oncogenes are sufficient in their own right to induce the expression of Slug, and that Slug is required for the biological activity of these oncogenes in cell invasion. As Slug is a protein implicated in the formation of the mesoderm (Nieto et al., 1994, cited above; Savagner et al., J. Cell Biology 137: 1403-1491 (1997)) and its expression is fairly uncontrolled (FIG. 2), it may have a more general role in the biology of the cancer than that associated specifically with transformation of BCR-ABL. Thus, expression of Slug could serve as a mechanism of cell invasion for fusion proteins found in other leukemias and proteins associated with sarcomas. In fact, expression of Slug is not rare in mesenchymal tumors (both leukemia or sarcoma) transformed under the auspices of other genetic alterations (Inukai et al., 1999; Khan et al., 1999, cited earlier), which suggests that Slug can be a component of the tumoral invasion, not only of leukemias positive for BCR-ABL, but also possibly of other mesenchymal cancers. Therefore, Slug appears to be a mechanism of tumoral invasion, both for leukemias and for sarcomas. In conclusion, with the present work, a mechanism has been established responsible for the invasive capacity of BCR-ABL and indications have been presented that suggest that Slug could represent a potentially broad tumoral invasion mechanism for mesenchymal tumors. Therefore, Slug itself could constitute an attractive target for treatment (it could be considered a marker of malignity) and therapeutic modulation of the invasive capacity in the treatment of human cancer.

Metastasis and Tumorigenicity may have the same Genetic Control

The leukaemic conversion of the tumoral target cells (Cobaleda et al., 2000; Sánchez-García, 2000, cited earlier) to cells with an autonomous growth state implies that certain specific genes have to be activated in order to decouple control of proliferation/differentiation and generate intracellular signals that can replace the requirements of the growth factors during invasion and cell dissemination. During the development of invasive tumors, the tumor cells disobey the social order of boundaries of organs and infiltrate foreign tissues. Only during transition of a tumor in situ to an invasive tumor, the tumor cells penetrate in the basal epithelial membrane and enter the underlying interstitial stroma, interacting with the stromatic cells. Thus, a definition of behavior of the metastatic tumor cells is the tendency to cross tissue compartment boundaries and intermix with different types of cell. The inventors have shown that BCR-ABL cells behave like metastatic tumor cells. It is assumed that blocking the differentiation is a consequence of the alteration of the properties of the chimeric fusion proteins (Sánchez-García, Annu. Rev. Genetics 31: 429-453 (1997)), BCR-ABL in the present case. It has been suspected that genes other than the oncogenes can produce metastasis that have been shown to be relevant for tumorigenesis. However, the results show clearly that transfection of BCR-ABL oncogenes into an appropriate receptor cell can induce the complete phenotype of tumorigenicity and invasion. These findings show that a fusion protein imposes an altered differentiation program on the target cell and a specific inductor agent of invasion that is required for the tumor cell to be transformed into an invasive cell. The model of the inventors also shows that the effecter genes of the invasion can be regulated independently of those that confer tumorigenicity by the same fusion gene, which represents a new oncogenic mechanism of action. Taking these data together, the idea is reinforced that transformation can be produced as a result of the creation/activation of a single oncogene (Sánchez-García, 1997, cited earlier). An interesting topic for future investigation will be identification of the factors that modulate expression of Slug and the possible implication of other oncoproteins that induce its expression.

Slug Associates Invasion and Tumoral Development

SLUG is a member of the Snail family of transcription factors with "zinc fingers" that play a conserved role from the evolutionary point of view in the formation of the mesoderm in invertebrates and vertebrates (Nieto et al., 1994, cited earlier). In chicken, Slug is expressed by ectodermal epithelial cells during their transition to mesenchymal cells. The chicken embryos treated with anti-sense oligonucleotide directed against Slug show inappropriate formation of the mesoderm related to defects in cellular migration in compartments of transition from epithelial cells to mesenchymal cells (Nieto et al., 1994, cited earlier). Thus, Slug induces cell migration in the epithelial-mesenchymal transition in the formation of the mesoderm and in the migration of cells from the neural crest (Fuse et al., Genes & Development 8, 2270-2281 (1994)). However, in mice, activation of the epithelial-mesenchymal transitions is under the control of Snail (Cano et al., Nature Cell Biology 2;: 76-83 (2000)), which allows migration from the primitive mesoderm in the form of epithelial cells. As a result, in mice without Slug, they develop normally (Jiang et al., Development Biology 18: 277-285 (1998)). In addition, it has been shown that the gene Snail activates the EMT associated with the acquisition of the invasive phenotype in solid epithelial tumors (Batlle et al., Nature Cell Biology 2: 84-89 (2000); Cano et al., 2000, cited earlier), where it contributes to the first event of the metastatic process. Thus, induction of EMT appears to be a function associated specifically with the Snail gene in mouse (Cano et al., 2000, cited earlier).

The data presented here show that Slug is an important regulator of the capacity of invasion during the progression of mesenchymal tumors in which the EMT are not required. This idea could be extended to the role of Slug in the acquisition on the part of parent mesenchymal cells of the capacity to migrate. In support of this theory, the experiments of the investigators indicate that, in vivo, Slug is not expressed in the peripheral blood of BCR-ABL transgenic mice with leukemia, defining an undifferentiated, pluripotent and migratory phenotype in the mesenchymal cells. Thus, it is conceivable that the presence of Slug is required in certain phases of normal development for an appropriate expansion and for the survival of the primitive haematopoietic cells (FIG. 8). At the same time, the results provide a molecular association between a regulator of the initial stages of development and the leukaemiogenesis, and offer clues for understanding the molecular alterations that lead to the invasive behavior of leukemias, in particular, and mesenchymal tumors, in general.

The invention claimed is:

1. A method for detecting invasiveness of cancer in a human subject, wherein said cancer is selected from the group consisting of t(9:22) leukemia, myeloid leukemia, T-cell leukemia or sarcoma, based on the aberrant expression of human Slug gene, wherein aberrant expression is over-expression of said gene or expression of said gene in cells that do not normally express said gene, which method comprises:
  1) identifying a human subject having any of said cancers;
  2) obtaining a test sample containing t(9:22) leukemia cells, myeloid leukemia cells, T-cell leukemia cells or sarcoma cells from said subject,
  3) evaluating the expression of the human Slug gene in said cancerous cells contained in said test sample by determining the level of mRNA corresponding to the Slug gene (SLUG mRNA); and
  4) comparing the expression of the human Slug gene in the cells of the test sample with the expression of the human Slug gene in the cells of a control sample;
  5) evaluating on the basis of the outcome of step (4) whether said cancer in said human subject is invasive, given that aberrant expression of the human Slug gene in the cells of the test sample, when compared with expression of the human Slug gene in cells of the control sample, is indicative of invasiveness of said cancerous cells in said test sample.

2. A method according to claim 1, in which said control sample is a biological sample of a human that does not have cancerous cells.

3. A method according to claim 1, in which the determination of the level of said human SLUG mRNA is performed by Northern blot analysis, mapping with S1 nuclease, polymerase chain reaction (PCR), retro-transcription in combination with polymerase chain reaction (RT-PCR), retro-transcription in combination with the ligase chain reaction (RT-LCR), hybridization or microarrays.

4. A method according to claim 1, wherein said cancer is t(9:22) leukemia and said cancerous cells are t(9:22) leukemia cells.

5. A method according to claim 1, wherein said cancer is myeloid leukemia and said cancerous cells are myeloid leukemia cells.

6. A method according to claim 1, wherein said cancer is T-cell leukemia and said cancerous cells are T-cell leukemia cells.

7. A method according to claim 1, wherein said cancer is sarcoma and said cancerous cells are sarcoma cells.

8. A method according to claim 1, wherein said control sample is a biological sample of a human that has cancerous cells.

* * * * *